United States Patent
Doppiu et al.

(10) Patent No.: US 9,834,572 B2
(45) Date of Patent: Dec. 5, 2017

(54) PROCESS FOR PREPARING HYDRIDOCARBONYLTRIS (TRIPHENYLPHOSPHINE)RHODIUM(I)

(71) Applicant: Umicore AG & Co. KG, Hanau-Wolfgang (DE)

(72) Inventors: Angelino Doppiu, Seligenstadt (DE); Ralf Karch, Kleinostheim (DE); Andreas Rivas-Nass, Bensheim (DE); Eileen Woerner, Nidderau (DE)

(73) Assignee: Umicore AG & Co. KG, Hanau-Wolfgang (DE)

( * ) Notice: Subject to any disclaimer, the term of this patent is extended or adjusted under 35 U.S.C. 154(b) by 0 days.

(21) Appl. No.: 15/324,017

(22) PCT Filed: Jul. 3, 2015

(86) PCT No.: PCT/EP2015/065200
§ 371 (c)(1),
(2) Date: Jan. 5, 2017

(87) PCT Pub. No.: WO2016/005282
PCT Pub. Date: Jan. 14, 2016

(65) Prior Publication Data
US 2017/0198000 A1    Jul. 13, 2017

(30) Foreign Application Priority Data

Jul. 11, 2014  (DE) .................. 10 2014 109 763

(51) Int. Cl.
*C07F 15/00*    (2006.01)
(52) U.S. Cl.
CPC ................. *C07F 15/0073* (2013.01)
(58) Field of Classification Search
CPC ....................................... C07F 15/00
USPC ........................................... 556/16
See application file for complete search history.

(56) References Cited

U.S. PATENT DOCUMENTS

| | | | |
|---|---|---|---|
| 2,644,446 | A | 7/1953 | Viniegra |
| 3,644,446 | A | 2/1972 | Booth et al. |
| 7,145,027 | B2 | 12/2006 | Walter et al. |

FOREIGN PATENT DOCUMENTS

| | | |
|---|---|---|
| EP | 0055487 A1 | 7/1982 |
| EP | 0083094 A1 | 7/1983 |
| WO | WO-2005005448 A1 | 1/2005 |

OTHER PUBLICATIONS

Ahmad et al., "Hydrido Phosphine Complexes of Rhodium(I)", Inorganic Syntheses, 1990, 28, 81-83.*

Bath, S., et al., "Five-Coordinate Hydrido-Carbonyl Complexes of Rhodium and Iridium and their Analogy with CoH(CO)$_4$", Communications to the Editor in Journal of the American Chemical Society, vol. 85, No. 21, (1963), pp. 3500-3501.
Ahmad, N., et al., "Hydrido Phosphine Complexes of Rhodium(I)", in Inorganic Syntheses: Reagents for Transition Metal Complex and Organometallic Syntheses, vol. 28 (ed R. J. Angelici), John Wiley & Sons, Inc.: Hoboken, NJ, USA, 1990, pp. 81-83.
Ahmad, N., et al., "Transition-metal Complexes Containing Phosphorus Ligands. Part VII. New and Improved Syntheses of Some Triphenylphosphine Complexes of Rhodium, Iridium, Ruthenium, and Osmium", Journal of the Chemical Society, Dalton Transactions, No. 7, (1972), pp. 843-847.
Dewhirst, K., et al., "The Preparation and Nuclear Magnetic Resonance Spectra of Hydridophosphine Complexes of Ruthenium and Rhodium", Inorganic Chemistry, vol. 7, No. 3, (1968), pp. 546-551.
Evans, D., et al., "trans-Carbonylchlorobis(Triphenyl-Phosphine)Rhodium and Related Complexes", in Inorganic Syntheses: Reagents for Transition Metal Complex and Organometallic Syntheses, vol. 28 (ed R. J. Angelici), John Wiley & Sons, Inc.: Hoboken, NJ, USA, 1990, pp. 79-80.
International Search Report for PCT/EP2015/065200 dated Sep. 17, 2015.
La Placa, S., et al., "Crystal and Molecular Structure of Tristriphenylphosphine Rhodium Carbonyl Hydride", Acta Crystallographica, vol. 18, (1965), pp. 511-519.
Leipoldt, J., et al., "The Crystal Structure of Acetylacetonatocarbonyltri-phenylphosphinerhodium(I)", Inorganica Chimica Acta, vol. 26, (1978), pp. L35-L37.
Levison, J., et al., "Transition-metal Complexes containing Phosphorus Ligands. Part III. Convenient Syntheses of Some Triphenylphosphine Complexes of the Platinum Metals", Journal of the Chemical Society A: Inorganic, Physical, Theoretical, (1970), pp. 2947-2954.
Varshavskii, Y., et al., "Rh(I) Carbonyl Carboxylato Complexes: Spectral and Structural Characteristics, Some Reactions of Coordinated Formate Group", Russian Journal of Coordination Chemistry, vol. 31, No. 2, (2005), pp. 121-131.

(Continued)

*Primary Examiner* — Sudhakar Katakam
*Assistant Examiner* — Kofi Adzamli
(74) *Attorney, Agent, or Firm* — Drinker Biddle & Reath LLP

(57) ABSTRACT

The present invention relates to a process for preparing hydridocarbonyltris(triphenylphosphine)rhodium(I), RhH(CO)(PPh$_3$)$_3$, also referred to hereinafter as "Rh-hydrido." An alcoholic suspension of triphenylphosphine is stirred with an Rh(III) chloride precursor at elevated temperature. The Rh(III) chloride precursor used may be rhodium(III) chloride hydrate RhCl$_3$*xH$_2$O or rhodium(III) chloride solution H$_3$[RhCl$_6$]*(H$_2$O)$_n$. After cooling, alcoholic alkali metal hydroxide solution is added, and the mixture is stirred for a few hours. Finally, sparging is effected with CO gas and the Rh-hydrido formed is removed. Rh-hydrido can be prepared by this process on the industrial scale with high yields and at very good quality.

13 Claims, No Drawings

(56) References Cited

OTHER PUBLICATIONS

Written Opinion of the International Searching Authority for PCT/EP2015/065200 dated Sep. 17, 2015.

\* cited by examiner

PROCESS FOR PREPARING HYDRIDOCARBONYLTRIS (TRIPHENYLPHOSPHINE)RHODIUM(I)

CROSS-REFERENCE TO RELATED APPLICATIONS

This application is a national stage application (under 35 U.S.C. §371) of PCT/EP2015/065200, filed Jul. 3, 2015, which claims benefit of German Application No. 10 2014 109 763.7, filed Jul. 11, 2014, both of which are incorporated herein by reference in their entirety.

INTRODUCTION

The subject-matter of the invention is a process for preparing hydridocarbonyltris(triphenylphosphine)rhodium (I), $RhH(CO)(PPh_3)_3$, hereinafter also referred to as "Rh-hydrido." "Ph" is used below as an abbreviation for the phenyl group.

The process is characterized by an improved single-step procedure which dispenses with any intermediate isolation or cleaning steps. It is therefore a so-called one-pot synthesis. In the present application, a process which may comprise several process steps but is carried out in a single container without intermediate, isolation steps is also referred to as "single-step," which should be understood in the sense of the one-pot synthesis described above.

With the single-step process, Rh-hydrido can be prepared with high yields and at a very high quality: The chloride content of the Rh-hydrido prepared by this process lies below 500 ppm (with respect to the product); the yield is higher than 99%. Furthermore, the volumetric yield in the preparation of Rh-hydrido by the process presented here is considerably higher than in the preparation by processes known from the prior art. This high volumetric yield means that the process is economically feasible on an industrial scale. Volumetric yield in this context means the quantity of product produced per unit volume in a reactor.

The Rh-hydrido prepared is especially suitable as a catalyst for homogeneous catalysis, such as in hydroformylation reactions, for example.

PRIOR ART

A number of one- and multi-step processes for preparing $RhH(CO)(PPh_3)_3$ are known from the prior art. The various syntheses known are shown below in diagrammatic form:

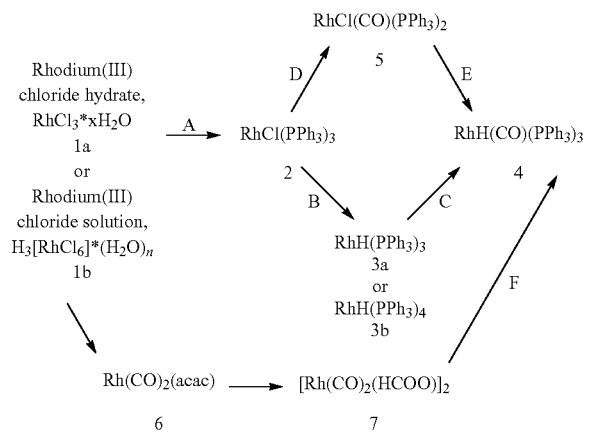

WO 2005/005448 A1 describes a process for preparing chlorotris(triphenylphosphine)rhodium(I) (2) by converting an Rh(III) chloride solution (1a and 1b) with triphenylphosphine. $RhCl(PPh_3)_3$ is known to the person skilled in the art by the name of "Wilkinson's catalyst." According to WO 2005/005448 A1, the quality of the product (2) is directly and reproducibly influenced by the temperature control during the reaction. The reaction solution must be heated slowly as otherwise very small, almost unfilterable Wilkinson's catalyst crystals will form. The process disclosed in WO 2005/005448 A1 yields chlorotris(triphenylphosphine) rhodium(I) (2) in the form of large crystals.

$RhCl(PPh_3)_3$ (2) formed in this way is only suitable to a limited extent for the synthesis of hydridocarbonyltris(triphenylphosphine)rhodium(I) (4) via the intermediate step 5 or 3. The large crystals are not readily soluble so that a full conversion to the intermediate product and to the product cannot be achieved. What is obtained is a mixture of reactant (2), intermediate products (5 and 3), and product (4). This means that greatly diluted solutions of (2) must be used. The volumetric yield of the product (4) is low.

The preparation of carbonylchlorobis(triphenylphosphine)rhodium(I) (5) from rhodium(III) chloride hydrate (1a) is disclosed in D Evans, J A Osborn, G Wilkinson, "trans-Carbonylchlorobis(triphenylphosphine)rhodium and related Complexes", Inorg Synth 1990, 28, 79-80. Here, an ethanolic solution of $RhCl_3*3H_2O$ (1a) is mixed with an excess of $PPh_3$, after which aqueous formaldehyde is quickly added. The yield (85%) and the volumetric yield (approx. 12 g/L) of $RhCl(CO)(PPh_3)2$ (5) are low, and the reaction product is very poorly soluble.

A one-pot reaction for preparing hydridocarbonyltris(triphenylphosphine)rhodium(I), $RhH(CO)(PPh_3)_3$ (4), from rhodium(III) chloride hydrate, $RhCl_3*3H_2O$ (1a), is disclosed in N Ahmad, S D Robinson, M Z Uttley, "Transition-metal Complexes Containing Phosphorus Ligands. Part VII. New and Improved Syntheses for Some Triphenylphosphine Complexes of Rhodium, Iridium, Ruthenium, and Osmium," J Chem Soc Dalton Trans 1972, 843-847 and in N Ahmad, J J Levison, S D Robinson, M F Uttley, "Hydrido Phosphine Complexes of Rhodium," Inorganic Synth 1990, 28, 81-83. A large molar excess of triphenylphosphine, aqueous formaldehyde solution and ethanolic KOH is added to an ethanolic solution of rhodium(III) chloride hydrate, $RhCl_3*3H_2O$, yielding $RhH(CO)(PPh_3)_3$. As an intermediate step $RhCl(CO)(PPh_3)_3$ (5) is formed. One disadvantage of this one-pot reaction is that it is not suitable for the industrial scale. The substances used must be in low concentrations as otherwise the intermediate step $RhCl(CO)$ $(PPh_3)_3$ (5) will not be fully converted and the product will contain too much Cl. An excessively high chlorine content will have a negative effect on the catalytic properties of the end product $RhH(CO)(PPh_3)_3$ (4). Furthermore, the reagents must be added in rapid succession to prevent the formation of by-products. However, in large-scale industrial production facilities, it is not possible to add reagents so quickly, which renders this process unsuitable for the industrial scale. In addition, the volumetric yield is low (approx. 6 g/L), which makes the process uneconomical.

In N Ahmad, S D Robinson, M Z Uttley, "Transition-metal Complexes Containing Phosphorus Ligands. Part VII. New and Improved Syntheses for Some Triphenylphosphine Complexes of Rhodium, Iridium, Ruthenium, and Osmium," J Chem Soc Dalton Trans 1972, 843-847 and in N Ahmad, J J Levison, S D Robinson, M F Uttley, "Hydrido Phosphine Complexes of Rhodium," Inorganic Syntheses Vol. 28, 1990, 81-83, a process is disclosed for preparing hydridotetrakis(triphenylphosphine)rhodium(I) (3b), in which rhodium chloride hydrate, $RhCl_3 \cdot 3H_2O$, (1a) is converted with triphenylphosphine to ethanolic KOH. Here, too, the components must be added quickly and the volumetric yield is low (approx. 9 g/L), which makes this process unsuitable for the industrial scale.

In J J Levison, S D Robinson, "Transition-metal Complexes containing Phosphorus Ligands. Part Ill. Convenient Syntheses of Some Triphenylphosphine Complexes of the Platinum Metals," J Chem Soc A 1970, 2947-2954, some processes for preparing hydridotetrakis(triphenylphosphine) rhodium(I) (3b) and hydridocarbonyltris(triphenylphosphine)rhodium(I) (4) are disclosed. In both cases, the reactant is rhodium(III) chloride hydrate, $RhCl_3 \cdot 3H_2O$, (1a). The conversion of $RhCl_3 \cdot 3H_2O$ with $PPh_3$ and $NaBH_4$ in ethanol yields $RhH(PPh_3)_4$. If in addition to $PPh_3$, $NaBH_4$ and ethanol, aqueous formaldehyde is also added to $RhCl_3 \cdot 3H_2O$, $RhH(CO)(PPh_3)_3$ (4) will be obtained. In both processes, the reactants must be added quickly and the volumetric yields are low (approx. 6 g/L), thus making them unsuitable for the industrial scale.

In K C Dewhirst, W Keim, C A Reilly, "The Preparation and Nuclear Magnetic Resonance Spectra of Hydridophosphine Complexes of Ruthenium and Rhodium," Inorg Chem 1968, 7, 546-551, the multi-step synthesis of $RhH(CO)(PPh_3)_3$ (4) is described. In the first step, the Wilkinson's catalyst (2) is converted into hydrido(triphenylphosphine)rhodium (3a) or (3b). In the second step, the carbonyl complex $RhH(CO)(PPh_3)_3$ is prepared therefrom. The reaction of $RhCl(PPh_3)_3$ (2) with aluminum triisopropyl in diethyl ether and n-hexane yields $RhH(PPh_3)_3$ (3a). If this reaction product (3a) is converted with $PPh_3$ in toluene, $RhH(PPh_3)_4$ (3b) is obtained. The reaction of $RhCl(PPh_3)_3$ (2) with $PPh_3$ and hydrazine in a benzene-ethanol mixture also produces $RhH(PPh_3)_4$ (3b). When (3a) is then converted with carbon monoxide in ethanol or (3b) is then converted with carbon monoxide in benzene, $RhH(CO)(PPh_3)_3$ (4) is produced. A disadvantage of the processes described by Dewhirst et al. is that they are not one-pot processes. The extremely air-sensitive intermediate products $RhH(PPh_3)_{3-4}$ (3a) and (3b) must be isolated. In addition, highly flammable or very toxic solvents or reagents, such as diethyl ether, toluene, benzene, aluminum triisopropyl and hydrazine are used. The product yield is markedly low (approx. 50%).

EP 0 055 487 B1 discloses a process for preparing a halocarbonylbis(triorganophosphorus) rhodium compound, which may, for example, be $RhCl(CO)(PPh_3)_2$ (5). Here, a solution consisting of (a) a rhodium complex concentrate, (b) a halide ion source, (c) carbon monoxide gas or a carbon monoxide source and (d) free triorganophosphorus ligands—$PPh_3$, for example—is converted. The rhodium complex concentrate consists of a spent hydroformylation reaction medium containing rhodium. Before the process begins, the hydroformylation reaction medium must be concentrated. The halocarbonylbis(triorganophosphorus) rhodium compound obtained can then optionally be converted in a one-pot process with a metal hydride and a triorganophosphorus ligand. The metal hydride will advantageously be a boron hydride and the triorganophosphorus ligand be $PPh_3$. Following conversion with metal hydride and triorganophosphorus ligand, a hydridocarbonyltris(triorganophosphorus) rhodium(I) compound, such as $RhH(CO)(PPh_3)_3$ (4), is obtained.

EP 0 083 094 B1 describes a one-step process for preparing a hydridocarbonyltris(triorganophosphorus) rhodium compound, which may, for example, be $RhCl(CO)(PPh_3)_3$ (5). Here, a solution consisting of (a) a rhodium complex concentrate, (b) hydrogen gas or a hydrogen source in the form of an alkali and/or alkali earth hydroxide, (c) an alcohol with 1 to 10 carbon atoms, (d) CO gas or a CO source, and (e) free triorganophosphorus ligands, such as $PPh_3$, is converted. The rhodium complex concentrate consists of a spent hydroformylation reaction medium containing rhodium. Before the process begins, the hydroformylation reaction medium must be concentrated. The product in the examples is described as a yellow-green suspension, which indicates a highly contaminated product. Another disadvantage is the moderate to poor yields of 13% to 75% in relation to the noble metal.

U.S. Pat. No. 3,644,446 describes a process, in which rhodium in a liquid reaction medium is mixed with an alkali metal hydroxide or alkali metal alkoxide, a reducing agent, such as hydrogen or carbon monoxide, and an alcohol in the presence of a ligand and brought to reaction at 0° C. to 150° C.

The melting points of the reaction products, which differ markedly from the actual melting point of $RhCl(CO)(PPh_3)_3$, indicate a highly contaminated product and, compared to the reactants, large quantities of solvents must be used. A particular sequence for adding substances or a particular temperature profile for the reaction is not described.

The volumetric yields are comparatively low not only in EP 0 055 487 B1 and U.S. Pat. No. 3,644,446 but also in EP 0 083 094 B1.

The preparation of acetylacetonato-dicarbonyl-rhodium (I) (6) from rhodium chloride trihydrate (1a) has been described in J G Leipoldt, S S Basson, L D C Bok, T L A Gerber, "The Crystal Structure of Acetylacetonatocarbonyl-triphenylphosphanerhodium (I)," Inorg Chim Acta 1978, 26, L35-L37. In the first step in this case, a solution of $[Rh_2Cl_2(CO)_4]$ was prepared by heating to reflux a solution of rhodium(III) chloride hydrate, $RhCl_3 \cdot 3H_2O$, in dimethylformamide. In the second step, acetylacetone was added, which caused $Rh(CO)_2(acac)$ (6) to form. Here "acac" stands for the acetylacetone group.

In Y S Varshavskii, T G Cherkasova, I S Podkorytov, A A Korlyukov, V N Khrustalev and A B Nikol'skii: "Rh(I) Carbonyl Carboxylato Complexes: Spectral and Structural Characteristics. Some Reactions of Coordinated Formate Group," Russ J Coord Chem 2005, 31, 121-131, the preparation of hydridocarbonyltris(triphenylphosphine)rhodium (I) (4) from dicarbonyl(acetylacetonato)rhodium(I) (6) is disclosed. In the first step, $Rh(CO)_2(acac)$ (6) is converted in diethyl ether with anhydrous formic acid to yield $[Rh(CO)_2(HCOO)]_2$ (7). In the second separate step, the formate complex (7) is converted with triphenylphosphine $PPh_3$ in the proportion 1:10 (mol/mol) in 2-propanol to yield $RhH(CO)(PPh_3)_3$ (4). This synthesis is unsuitable for large-scale applications since the highly flammable diethyl ether is used in the first step and a large surplus of $PPh_3$ is required in the second step. This is, furthermore, a complex multi-step synthesis.

The previously known processes for preparing hydridocarbonyltris(triphenylphosphine)rhodium(I) have numerous disadvantages: Some processes have multiple steps and require the complex isolation of intermediate products. Although other processes have but one step, they cannot be used on the industrial scale since the reactants must be rapidly added and the speed at which substances can be added in large-scale installations is limited. What all known processes have in common is that the volumetric yield—that is, the mass of product per unit of volume of solvent—is relatively low, which means that large quantities of solvents must be used and then have to be removed again.

The task of the present invention is therefore to overcome the disadvantages of the prior art in the preparation of RhHCO(PPh$_3$)$_3$ and to provide a process that not only runs in a single step but is also feasible on the industrial scale with a significantly improved volumetric yield.

This task is solved by a single-step process for preparing RhH(CO)(PPh$_3$)$_3$, comprising the steps:
(a) Preparation of an alcoholic suspension of triphenylphosphine PPh$_3$ in an inerted reaction vessel,
(b) Mixing the alcoholic PPh$_3$ suspension with an Rh(III) chloride precursor at a temperature of 30 to 40° C.,
(c) Stirring the reaction mixture of PPh$_3$ suspension and Rh(III) chloride precursor at an elevated temperature, in one embodiment for 1.5 to 3 hours,
  wherein stirring is carried out with reflux if the boiling point of the alcohol is below 85° C., or
  wherein stirring is carried out with the reaction vessel having an internal temperature of 75° C. to 85° C. if the boiling point of the alcohol is 85° C. or higher,
(d) Cooling the suspension from step (c) down to 35-50° C., in particular to 40-50° C.,
(e) Adding an alcoholic alkali hydroxide solution,
(f) Stirring the reaction suspension at 35-50° C., in particular at 40-50° C., wherein a duration of 1.5 to 3 hours is in most cases sufficient,
(g) Sparging with CO gas, in most cases for 2 to 16 hours,
(h) Separating and if applicable washing and drying the hydridocarbonyltris(triphenylphosphine)rhodium(I) complex.

Solving the task comprises the provision of a one-step process for the preparation of hydridocarbonyltris(triphenylphosphine)rhodium(I). The process is environmentally friendly and economical due to the chemicals used, the process control, the high product quality, and the high yields achievable, including the volumetric yield.

A one-step process within the meaning of the present invention comprises the preparation of hydridocarbonyltris(triphenylphosphine)rhodium(I) without any isolation of intermediate products. The present invention therefore describes a process, in which the target product is prepared from the starting materials in situ in a single reactor without costly and time-consuming intermediate isolation steps or intermediate cleaning steps. This in-situ preparation in a single reactor without intermediate isolation steps or intermediate cleaning steps is hereinafter referred to as "one-pot synthesis."

This process makes a simple isolation of the hydridocarbonyltris(triphenylphosphine)rhodium(I) possible since process conditions have been deliberately selected, in which the target compound precipitates directly from the reaction mixture. The process thus comprises the formation of a suspension, which contains the separable compound as a precipitate. No time-consuming or costly isolation, for example, by separating, concentrating or by other processes is thus necessary.

The process for preparing hydridocarbonyltris(triphenylphosphine)rhodium(I) is explained below, wherein the invention comprises all embodiments listed below either individually or in combination with each another.

In step (a) of the process described here, an alcoholic suspension of triphenylphosphine PPh$_3$ is prepared. In order to prepare this suspension, primary and secondary alcohols with one to five carbon atoms are used. This may be one or more primary alcohols, one or more secondary alcohols or mixtures of at least one primary and at least one secondary alcohol.

Here, the alcohol is selected from methanol, ethanol, n-propanol, 2-propanol, n-butanol, 2-methyl-1-propanol (isobutanol), 2-butanol, 1-pentanol, 2-pentanol, 3-pentanol, 2-methyl-1-butanol, 3-methyl-1-butanol, 3-methyl-2-butanol, 2,2-dimethyl-1-propanol and mixtures of these alcohols. The alcohols used for preparing the suspension of triphenylphosphine are hereinafter referred to as "the alcohol." Here, "the alcohol" can represent a single alcohol or a mixture of several alcohols.

In one specific embodiment, the alcohol is selected from methanol, ethanol, n-propanol and 2-propanol and mixtures of at least two of these alcohols. Ethanol is very suitable.

Before being filled with alcohol, the reaction vessel is inerted. Here, "inerting" is understood to be the expulsion of the oxygen in the vessel by an inert gas, such as argon or nitrogen. The mixture of PPh$_3$ and alcohol will advantageously contain 100 to 250 g of PPh$_3$ per liter of alcohol, in particular 150 to 220 g of PPh$_3$ per liter.

The alcohol is put into the inerted reaction vessel, PPh$_3$ is added, and the alcohol-PPh$_3$ mixture is heated. If the boiling point of the alcohol is below 85° C., it is heated to its boiling point. In the case of alcohols with a boiling point of 85° C. or above, heating is applied until the reaction vessel has an internal temperature of 75° C. to 85° C. The person skilled in the art knows the boiling points of the alcohols mentioned above.

Once this temperature has been reached, stirring at reflux is carried out for 15 to 60 min, advantageously for 30 min, if heating was previously effected up to the boiling point of the alcohol. If the boiling point of the alcohol used is higher than 85° C., once the internal temperature of the reactor vessel has reached 75° C. to 85° C., stirring is carried out at this temperature for 15 to 60 min, advantageously for 30 min. Depending on the quantity of PPh$_3$ used per liter of alcohol and on the type of alcohol, all or the great majority of the PPh$_3$ will dissolve in the alcohol. The reaction mixture is then cooled down to an internal temperature $T_{internal}$ of 30° C. to 40° C., advantageously to 35° C. Here, some of the PPh$_3$ can precipitate again as a fine powder. Once the reaction mixture has cooled down to 30° C. to 40° C., the result is a PPh$_3$ suspension.

According to the textbooks, a dispersion is a mixture of at least two mutually immiscible phases, where one of the at least two phases is liquid. Depending on the aggregate state of the second or further phase, dispersions are divided into aerosols, emulsions and suspensions, where the second or further phase is gaseous in the case of aerosols, liquid in the case of emulsions, and solid in the case of suspensions. In the process, once the reaction mixture has cooled down to 30° C. to 40° C., the result is a PPh$_3$ suspension.

In step (b) of the process, the alcoholic PPh$_3$ suspension is mixed with an Rh(III) chloride precursor. The Rh(III) chloride precursor is selected from rhodium(III) chloride hydrate, RhCl$_3$*xH$_2$O, and rhodium(III) chloride solution, H$_3$[RhCl$_6$]*(H$_2$O)$_n$, aqueous and alcoholic solutions of RhCl$_3$*xH$_2$O and H$_3$[RhCl$_6$]*(H$_2$O)$_n$ as well as mixtures of thereof. The term "alcohol" is used here as in the definition given for the PPh$_3$ suspension. The term "aqueous and alcoholic solutions of RhCl$_3$*xH$_2$O and H$_3$[RhCl$_6$]*(H$_2$O)$_n$ as well as mixtures thereof" here includes the following:
(a) Aqueous solutions, which contain either or both of the substances RhCl$_3$*xH$_2$O and H$_3$[RhCl$_6$]*(H$_2$O)$_n$,
(b) Alcoholic solutions, which contain either or both of the substances RhCl$_3$*xH$_2$O and H$_3$[RhCl$_6$]*(H$_2$O)$_n$,
(c) Solutions, which contain water and alcohol and either or both of the substances RhCl$_3$*xH$_2$O and H$_3$[RhCl$_6$]*(H$_2$O)$_n$, In one specific embodiment, a solution as defined in (b) is used.

In another specific embodiment, a solution as defined in (c) is used.

If the solutions contain alcohol in accordance with (b) or (c), there can be one single alcohol or a mixture of at least two alcohols. In another embodiment, the alcohol is selected from methanol, ethanol, n-propanol and 2-propanol and mixtures thereof. Ethanol is very suitable.

It is known to the person skilled in the art that Rh(III) chloride hydrate and Rh(III) chloride solution are not defined compounds with an exact stoichiometric composition. The formulas $RhCl_3*xH_2O$ and $H_3[RhCl_6]*(H_2O)_n$ therefore represent idealized compositions. The present complex compounds change depending upon the halide and water content of the compounds. Rhodium(III) chloride hydrate and its commercially available aqueous solution are normally present as mixed chloro-aquo complexes, which is the reason why the water content in the idealized formula is given as "$xH_2O$." Depending upon the preparation process for rhodium(III) chloride hydrate and rhodium(III) chloride solution, more or fewer aquo or chloride ligands are bound to the rhodium(III) complex. In the preparation of a solid phase of Rh(III) chloride hydrate, this depends upon the degree of evaporation, and, in the preparation of a solution, it depends upon the acid content (HCl) and the concentration of this solution.

The Rh(III) chloride precursors, rhodium(III) chloride hydrate, $RhCl_3*xH_2O$, and rhodium(III) chloride solution, $H_3[RhCl_6]*(H_2O)n$, which are to be used, are commercially available. In general, all rhodium(III) chloride hydrates and rhodium(III) chloride solutions can be used for this process, namely independently of their respective water or chloride content (Rh/Cl ratio), provided that these rhodium chloride hydrates are completely soluble in alcohol, water or mixtures thereof.

In one advantageous embodiment, the rhodium(III) chloride precursor is selected from a rhodium(III) chloride hydrate with a maximum rhodium content of 40% and rhodium(III) chloride solutions with a rhodium content of approx. 20% and a chlorine/rhodium ratio of 4:1 to 6:1.

In a further specific embodiment, the Rh(III) chloride precursor is $RhCl_3*3H_2O$. This compound is hereinafter also referred to as "rhodium(III) chloride hydrate."

In a further specific embodiment, the Rh(III) chloride precursor is $H_3[RhCl_6]*_n(H_2O)$, which is referred to below as "rhodium(III) chloride solution." Typically, aqueous rhodium(III) chloride solutions with a rhodium content of less than 30 wt % are used since they are available commercially and prepared, for example, by dissolving rhodium metal in the presence of concentrated hydrochloric acid and chlorine gas. However, suitable rhodium(III) chloride solutions may also be diverted from process streams in precious metal recycling or in industrial precious metal chemistry. Furthermore, the use of a rhodium(III) chloride solution, as opposed to the commonly used solid rhodium(III) chloride hydrate, has the advantage of offering more cost-effective and faster processing, since upstream evaporation, isolation as rhodium(III) chloride hydrate, and analysis to determine the starting quantity are not required.

In one advantageous embodiment of the present invention, the alcoholic $PPh_3$ suspension is mixed with an Rh(III) precursor as per step (b) of the process without the Rh(III) precursor being previously mixed with a solvent. Although the Rh(III) precursors with the idealized compositions $RhCl_3*xH_2O$ and $H_3[RhCl_6]*(H_2O)_n$ do themselves have a certain water content, in the embodiment mentioned here, no further solvent is added to this water before mixing with the $PPh_3$ suspension is carried out.

In a further embodiment, the Rh(III) precursor is added to a solvent before it is mixed with the $PPh_3$ suspension in accordance with step (b) of the process. This solvent is water, an alcohol or mixtures thereof in accordance with the definition given above. If the Rh(III) precursor is a rhodium (III) chloride solution, the precursor in one specific embodiment is mixed with an alcohol.

The ready Rh(III) precursor solution advantageously has a rhodium content of 10-30 wt %, or 15-20 wt %, this figure relating to pure rhodium. In the present invention, the term "pure rhodium" relates exclusively to rhodium or rhodium ions in a compound, other elements involved in the compound being ignored.

The $PPh_3$ suspension and Rh(III) chloride precursor are mixed for a period of 0.5 to 3 hours, in particular for 0.5 to 1 hour.

In doing so, the $PPh_3$ suspension and Rh(III) chloride precursor are mixed together in the proportions 4:1 to 10:1 (mol/mol), or 4:1 to 6:1 with respect to the quantities of $PPh_3$ and pure rhodium. Mixing can in this case be continuous or discontinuous. Continuous mixing is understood in that the $PPh_3$ suspension and Rh(III) chloride precursor are added simultaneously to a mixing vessel over a period of 1-3 hours. Discontinuous mixing is understood in that all of one mixing component is added first, after which the other mixing component is added.

In one advantageous embodiment, the Rh(III) chloride precursor is added to the $PPh_3$ suspension already present.

In all of the continuous and discontinuous mixing processes described above, mixing takes place in an inerted reactor.

Once the $PPh_3$ suspension and Rh(III) chloride precursor have been mixed, the resultant reaction mixture is stirred at reflux for 1.5 to 3 hours, or for 2 hours, in accordance with step (c) of the process. It is then, in accordance with step (d), cooled to 35° C. to 50° C. or 40° C. to 50° C., in particular to 45° C. Here, the same applies as in step (a), that in the case of a boiling point of the alcohol below 85° C., heating is applied up to that boiling point and stirring then carried out with reflux. In the case of alcohols with a boiling point above 85° C., heating is applied until the reaction vessel has an internal temperature of 75° C. to 85° C. The person skilled in the art knows the boiling points of the alcohols mentioned above. Once the boiling point temperature has been reached or the internal temperature has reached 75° C. to 85° C., the mixture is stirred at this temperature for the time specified.

Upon completion of step (d), an alcoholic alkali hydroxide solution is then added at this temperature of 35° C. to 50° C. as specified in step (e). This can take place over a period of 0.5-3 hours, in particular 1 hour. Suitable alcohols are methanol, ethanol and 2-propanol as well as mixtures thereof, in particular ethanol. Suitable alkali hydroxides are NaOH and KOH, with KOH being advantageous. The alcoholic alkali hydroxide solution is particularly advantageously an ethanolic potassium hydroxide solution since KOH is highly soluble in ethanol. The concentration of the alkali hydroxide in the alcoholic solution is advantageously 3.8 to 6 mol/L or 4 to 5 mol/L.

Advantageously, 7 to 12 equivalents of alkali hydroxide are added per equivalent of pure rhodium. On the basis of his technical knowledge, the person skilled in the art can see that the amount of alkali hydroxide required depends on the acid content of the rhodium(III) chloride precursor: The higher the content the more alkali hydroxide is required.

Once the alcoholic alkali hydroxide solution has all been added, the reaction mixture is stirred again at 35° C. to 50° C. in accordance with step (f). This can be done for a period of 1.5-3 hours.

The same or different alcohols can be used for preparing the alcoholic PPh$_3$ suspension and the alcoholic alkali hydroxide solution. Using the same alcohol in preparing both alcoholic solutions has proven effective. If the Rh(III) chloride precursor is dissolved in an alcohol before the PPh$_3$ suspension is added, the same alcohol can advantageously also be used for this as for the preparation of the PPh$_3$ suspension and the alcoholic alkali hydroxide solution.

The suspension is then sparged with carbon monoxide. CO sparging can be carried out at normal pressure or under pressure. In the case of sparging under pressure, a pressure of about 0.1 MPa (1 bar) is recommended. The sparging time is 2 to 16 hours. On the basis of his technical knowledge, the person skilled in the art can see that the required sparging time depends on the pressure selected: The higher the pressure the shorter the sparging time required. If sparging is at normal pressure, CO gas sparging times of 8 to 16 hours are advantageous. When sparging at a pressure of about 0.1 MPa (1 bar), a sparging time of 2 to 4 hours suffices. In the case of CO sparging under pressure, the pressure is subsequently released.

Upon completion of CO sparging, the reaction vessel is flushed free of CO by an inert gas. Suitable inert gases are, for example, argon and nitrogen. The reaction product RhH(CO)(PPh$_3$)$_3$ is then separated, washed and dried. Separation is advisably carried out by filtration, in particular extraction by suction at reduced pressure. Advantageously, extraction is carried out in an inert atmosphere.

Advantageously, the product is then washed with an alcohol, in particular with methanol, ethanol, 2-propanol or a mixture thereof. In particular, the alcohol used for washing is the same one as was also used for preparing the solutions of PPh$_3$ and the alcoholic alkali hydroxide solution. If more than one alcohol was used for preparing the said two solutions, for example, ethanol for PPh$_3$ and methanol for the alkali hydroxide, it is advantageous to use ethanol or methanol for washing the end product but not any further alcohol, such as 2-propanol.

Finally, the reaction product RhH(CO)(PPh$_3$)$_3$ is washed free of chloride with demineralized water.

In other words, the end product, RhH(CO)(PPh$_3$)$_3$, can be washed with an alcohol, water or a combination thereof. The product is then dried.

With the aid of this process, hydridocarbonyltris(triphenylphosphine)rhodium(I) can be prepared in a one-step process with a high volumetric yield. Unlike previously known processes, the new process is suitable for preparing RhH(CO)(PPh$_3$)$_3$ on the industrial scale since no poorly soluble intermediate products are created and substances can be added slowly, which is a precondition of production in large-scale reaction vessels.

EXEMPLARY EMBODIMENTS

Exemplary Embodiment 1: Preparation of carbonylhydridotris(triphenylphosphine)rhodium(I) from Rh Chloride Solution on the 10 L Scale Idealized Reaction Equations:

$$H_3[RhCl_6]*(H_2O)_n + 4PPh_3 \rightarrow RhCl(PPh_3)_3 + 5HCl + OPPh_3$$

$$RhCl(PPh_3)_3 + KOH + CH_3CH_2OH + PPh_3 \rightarrow RhH(PPh_3)_4 + KCl + CH_3CHO + H_2O$$

$$RhH(PPh_3)_4 + CO \rightarrow RhH(CO)(PPh_3)_3 + PPh_3$$

A 10 L double-jacketed reactor with a 2-level stirrer, reflux condenser and a gas inlet is inerted with inert gas. With the stirrer revolving at 150 rpm, 6 L ethanol are added. Afterwards, 1.2 kg (4.575 mol) triphenylphosphine (at least 99.5%, manufactured by BASF) are transferred into the reactor. The PPh$_3$ container is rinsed into the reactor with 50 mL ethanol. The stirrer speed is set to 260 rpm, the cooling water turned on, and the reactor heated to reflux. The mixture is stirred for 30 minutes at reflux. The PPh$_3$ dissolves completely. The solution is then cooled to T$_{internal}$: 35° C., where the PPh$_3$ can again partially precipitate as a fine powder. Afterwards, 105 g rhodium (1.02 mol) in the form of approx. 525 g aqueous Rh(III) chloride solution (Umicore product no. 68.2565.2720; Rh content approx. 20 wt %) are added. The container with rhodium chloride solution is rinsed into the reactor with 100 mL ethanol. The reaction mixture is then heated once again to reflux (T$_{internal}$: 76-78° C.) and maintained at reflux for 2 hours. The result is a red suspension with a fine precipitate.

At the end of the 2 hours, the reaction suspension is cooled to T$_{internal}$: 45° C. At this temperature, an ethanolic potassium hydroxide solution (10.3 eq., 10.5 mol potassium hydroxide pellets corresponding to 591 g pure KOH dissolved in 2.2 L ethanol) is added over 0.5 hour by means of a dropping funnel with gas equalization. The KOH-EtOH container and the dropping funnel are rinsed with 0.5 L ethanol into the reactor. The suspension, now yellow, is stirred for 2 hours at T$_{internal}$: 45° C. CO gas is then led over the reaction mixture at normal pressure. Sparging is continued for 8 to 16 hours. During this period, the reactor is cooled to T$_{internal}$: 20° C.

Following conversion, CO sparging is interrupted and the reactor flushed free of CO with argon or nitrogen. The yellow suspension is discharged inertly onto D4 glass funnel filters and dried by suction. The suspension is then washed with 0.5 L ethanol. After the ethanol is removed by suction at reduced pressure, the filter cake is washed free of chloride with (demineralized) water. The solid substance is then dried in the vacuum drying cabinet at 40° C. until a constant weight is achieved.

The result is approx. 927 g of yellow, crystalline solid with approx. 11.2% rhodium. This is equivalent to a metal-based yield of ~99% and a volumetric yield of approx. 104 g/L.

The identity of the product RhH(CO)(PPh$_3$)$_3$ is determined by $^1$H- and $^{31}$P-NMR spectroscopy in toluene and also by an IR spectrum. Purity is determined by CHN elemental analysis and by quantitative $^{31}$P-NMR analysis. The content of rhodium and phosphorus is determined by ICP-OES. The total chlorine content is under 200 ppm (chlorine analyzer).

Exemplary Embodiment 2: Preparation of carbonylhydridotris(triphenylphosphine)rhodium(I) from rhodium(III) Chloride Hydrate Idealized Reaction Equations:

$$RhCl_3*xH_2O + 4PPh_3 \rightarrow RhCl(PPh_3)_3 + 2HCl + OPPh_3$$

$$RhCl(PPh_3)_3 + KOH + CH_3CH_2OH + PPh_3 \rightarrow RhH(PPh_3)_4 + KCl + CH_3CHO + H_2O$$

$$RhH(PPh_3)_4 + CO \rightarrow RhH(CO)(PPh_3)_3 + PPh_3$$

A 10 L double-jacketed reactor with a 2-level stirrer, reflux condenser and a gas inlet is inerted with inert gas. With the stirrer revolving at 150 rpm, 6 L ethanol are added. Afterwards, 936 g (3.57 mol) triphenylphosphine (at least 99.5%, manufactured by BASF) are transferred into the reactor. The PPh$_3$ container is rinsed into the reactor with 50 mL ethanol. The stirrer speed is set to 260 rpm, the cooling water turned on, and the reactor heated to reflux. The mixture is stirred for 30 minutes at reflux. The PPh$_3$ dissolves completely. The solution is then cooled to T$_{internal}$: 35° C., where the PPh$_3$ can again partially precipitate as a fine powder. Afterwards, 85 g rhodium (0.83 mol) in the form of approx. 224 g rhodium(III) chloride hydrate (Umicore product no. 68.2562.1138; Rh content approx. 38 wt %) are added. The container with rhodium chloride solution is rinsed into the reactor with 50 mL ethanol. The reaction mixture is then heated once again to reflux (T$_{internal}$: 76-78° C.) and maintained at reflux for 2 hours. The result is a red suspension with a fine precipitate. At the end of the 2 hours, the reaction suspension is cooled to T$_{internal}$: 45° C. At this temperature, an ethanolic potassium hydroxide solution (8.3 eq., 6.9 mol potassium hydroxide pellets corresponding to 386 g pure KOH dissolved in 1.4 L ethanol) is slowly added over 0.5 hour by means of a dropping funnel with gas equalization. The KOH-EtOH container and the dropping funnel are rinsed with 1.4 L ethanol into the reactor. The suspension, now yellow, is stirred for 2 hours at T$_{internal}$: 45° C. CO gas is then led over the reaction mixture at normal pressure. Sparging is continued for 8 to 16 hours. During this period, the reactor is cooled to T$_{internal}$: 20° C. Conversion with CO can also be carried out under pressure in a pressure reactor. The recommendation here is approx. 0.1 MPa (1 bar) (uninterrupted—in other words, readjustment is necessary) for approx. 2-4 h. Afterwards, following pressure relief, the procedure is as follows. Following conversion, CO sparging is interrupted and the reactor flushed free of CO with argon or nitrogen. The yellow suspension is discharged inertly onto D4 glass funnel filters and dried by suction. The suspension is then washed with 0.5 L ethanol. After the ethanol is removed by suction at reduced pressure, the filter cake is washed free of chloride with (demineralized) water. The solid substance is then dried in the vacuum drying cabinet at 40° C. until a constant weight is achieved.

The result is approx. 754 g of yellow, crystalline solid with approx. 11.2% rhodium. This is equivalent to a metal-based yield of ~99% and a volumetric yield of approx. 85 g/L.

The identity of the product RhH(CO)(PPh$_3$)$_3$ is determined by $^1$H- and $^{31}$P-NMR spectroscopy in toluene and also by an IR spectrum. Purity is determined by CHN elemental analysis and by quantitative $^{31}$P-NMR analysis. The content of rhodium and phosphorus is determined by ICP-OES. The total chlorine content is under 150 ppm (chlorine analyzer).

Exemplary Embodiment 3: Preparation of carbonylhydridotris(triphenylphosphine)rhodium(I) from Rhodium Chloride Solution on the 1 L Scale in Isopropyl Alcohol (2-propanol)

Idealized Reaction Equations:

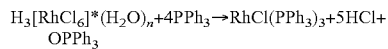

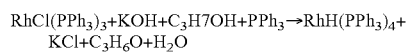

A 1 L double-jacketed reactor with a 2-level stirrer, reflux condenser and a gas inlet is inerted with inert gas. With the stirrer revolving at 150 rpm, 650 mL isopropyl alcohol are added. Afterwards, 107 g (0.4 mol) triphenylphosphine (at least 99.5%, manufactured by BASF) are transferred into the reactor. The PPh$_3$ container is rinsed into the reactor with 5 mL isopropyl alcohol. The stirrer speed is set to 260 rpm, the cooling water turned on, and the reactor heated to reflux. The mixture is stirred for 30 minutes at reflux. The PPh$_3$ dissolves completely. The solution is then cooled to T$_{internal}$: 35° C., where the PPh$_3$ partially precipitates as a fine powder. Afterwards, 9.25 g rhodium (0.090 mol) in the form of approx. 47 g aqueous Rh(III) chloride solution (Umicore product no. 68.2565.2720; Rh content approx. 20 wt %) are added. The container with rhodium chloride solution is rinsed into the reactor with 10 mL isopropyl alcohol. The reaction mixture is then heated once again to reflux (T$_{internal}$: 78.5° C.) and maintained at reflux for 2 hours. The result is a red suspension with a fine precipitate.

At the end of the 2 hours, the reaction suspension is cooled to T$_{internal}$: 45° C. At this temperature, an ethanolic potassium hydroxide solution (10.3 eq., 1.05 mol potassium hydroxide pellets corresponding to 52 g pure KOH dissolved in 230 mL ethanol) is added over 0.5 hour by means of a dropping funnel with gas equalization. The KOH-EtOH container and the dropping funnel are rinsed with 50 mL ethanol into the reactor. The suspension, now yellow, is stirred for 2 hours at T$_{internal}$: 45° C. CO gas is then led over the reaction mixture at normal pressure. Sparging is continued for 8 to 16 hours. During this period, the reactor is cooled to T$_{internal}$: 20° C.

Following conversion, CO sparging is interrupted and the reactor flushed free of CO with argon or nitrogen. The yellow suspension is discharged inertly onto D4 glass funnel filters and dried by suction. The suspension is then washed with 50 mL ethanol. After the ethanol is removed by suction at reduced pressure, the filter cake is washed free of chloride with (demineralized) water. The solid substance is then dried in the vacuum drying cabinet at 40° C. until a constant weight is achieved.

The result is approx. 80 g of yellow, crystalline solid with approx. 11.2% rhodium. This is equivalent to a metal-based yield of ~97% and a volumetric yield of approx. 80 g/L.

The identity of the product RhH(CO)(PPh$_3$)$_3$ is determined by $^1$H- and $^{31}$P-NMR spectroscopy in toluene and also by an IR spectrum. Purity is determined by CHN elemental analysis and by quantitative $^{31}$P-NMR analysis. The content of rhodium and phosphorus is determined by ICP-OES. The total chlorine content is under 200 ppm (chlorine analyzer).

Exemplary Embodiment 4: Preparation of carbonylhydridotris(triphenylphosphine)rhodium(I) from Rhodium Chloride Solution on the 1 L Scale with Sparging Under Pressure Idealized Reaction Equations:

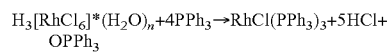

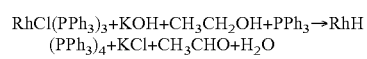

A 1 L double-jacketed pressure reactor with a 2-level stirrer, reflux condenser and a gas inlet is inerted with inert gas. With the stirrer revolving at 150 rpm, 600 mL ethanol are added. Afterwards, 120 g (0.4575 mol) triphenylphosphine (at least 99.5%, manufactured by BASF) are transferred into the reactor. The PPh$_3$ container is rinsed into the reactor with 5 mL ethanol. The stirrer speed is set to 260 rpm, the cooling water turned on, and the reactor heated to reflux. The mixture is stirred for 30 minutes at reflux. The PPh$_3$ dissolves completely. The solution is then cooled to T$_{internal}$: 35° C., where the PPh$_3$ can again partially precipitate as a fine powder. Afterwards, 10.5 g rhodium (0.102 mol) in the form of approx. 52.5 g aqueous Rh(III) chloride solution (Umicore product no. 68.2565.2720; Rh content approx. 20 wt %) are added. The container with rhodium chloride solution is rinsed into the reactor with 10 mL ethanol. The reaction mixture is then heated once again to reflux (T$_{internal}$: 76-78° C.) and maintained at reflux for 2 hours. The result is a red suspension with a fine precipitate.

At the end of the 2 hours, the reaction suspension is cooled to T$_{internal}$: 45° C. At this temperature, an ethanolic potassium hydroxide solution (10.3 eq., 1.05 mol potassium hydroxide pellets corresponding to 59.1 g pure KOH dissolved in 22:0 mL ethanol) is added over 0.5 hour by means of a dropping funnel with gas equalization. The KOH-EtOH container and the dropping funnel are rinsed with 50 mL ethanol into the reactor. The suspension, now yellow, is stirred for 2 hours at T$_{internal}$: 45° C. CO gas at an overpressure of 0.1 MPa (1 bar) is then pressed onto the reaction. The pressure is maintained at 0.1 MPa (1 bar) for 2-4 hours by adjustment of the CO gas. At the end of sparging (but no later than 4 h), the reactor is cooled to T$_{internal}$: 20° C. The CO feed is interrupted and pressure released from the reactor. Next, the reactor is flushed free of CO with argon or nitrogen.

The yellow suspension is discharged inertly onto D4 glass funnel filters and dried by suction. The suspension is then washed with 50 mL ethanol. After the ethanol is removed by suction at reduced pressure, the filter cake is washed free of chloride with (demineralized) water. The solid substance is then dried in the vacuum drying cabinet at 40° C. until a constant weight is achieved.

The result is approx. 92.7 g of yellow, crystalline solid with approx. 11.2% rhodium. This is equivalent to a metal-based yield of ~99% and a volumetric yield of approx. 104 g/L.

The identity of the product RhH(CO)(PPh$_3$)$_3$ is determined by $^1$H- and $^{31}$P-NMR spectroscopy in toluene and also by an IR spectrum. Purity is determined by CHN elemental analysis and by quantitative $^{31}$P-NMR analysis. The content of rhodium and phosphorus is determined by ICP-OES. The total chlorine content is under 200 ppm (chlorine analyzer).

The invention claimed is:

1. A one-step process for preparing RhH(CO)(PPh$_3$)$_3$, comprising these steps:
    (a) Preparing an alcoholic suspension of triphenylphosphine PPh$_3$ in an inerted reaction vessel,
    (b) Mixing the alcoholic PPh3 suspension with an Rh(III) chloride precursor at a temperature of 30 to 40° C.,
    (c) Stirring the reaction mixture of PPh$_3$ suspension and Rh(III) chloride precursor at an elevated temperature,
        wherein stirring is carried out with reflux if the boiling point of the alcohol is below 85° C., or
        wherein stirring is carried out with the reaction vessel having an internal temperature of 75° C. to 85° C. if the boiling point of the alcohol is 85° C. or higher,
    (d) Cooling the suspension from step (c) down to 35-50° C.,
    (e) Adding an alcoholic alkali hydroxide solution,
    (f) Stirring the reaction suspension at 35-50° C.,
    (g) Sparging with CO gas,
    (h) Separating and optionally washing and drying the hydridocarbonyltris(triphenylphosphine)rhodium(I) complex, RhH(CO)(PPh$_3$)$_3$.

2. The process according to claim 1, wherein the Cooling of the suspension from step (c) down to 40-50° C., and the Stirring the reaction suspension at 40-50° C.

3. The process according to claim 1, wherein the Rh(III) chloride precursor being selected from rhodium(III) chloride hydrate, RhCl$_3$*xH$_2$O, rhodium(III) chloride solution H$_3$[RhCl$_6$]*(H$_2$O)$_n$, aqueous or alcoholic solutions of RhCl$_3$*xH$_2$O or H$_3$[RhCl$_6$]*(H$_2$O)$_n$ or mixtures thereof.

4. The process according to claim 2, wherein the alcohol for preparing alcoholic solutions of RhCl$_3$*xH$_2$O and H$_3$[RhCl$_6$]*(H$_2$O)$_n$ and also mixtures of aqueous and alcoholic solutions of RhCl$_3$*xH$_2$O and H$_3$[RhCl$_6$]*(H$_2$O)$_n$ is selected from the group consisting of methanol, ethanol, n-propanol, 2-propanol and mixtures thereof.

5. The process according to claim 1, wherein the alcohol for preparing the solutions of PPh$_3$ and the alkali hydroxide solution is selected from the group consisting of methanol, ethanol, n-propanol, 2-propanol and mixtures thereof.

6. The process according to claim 1, wherein the alkali hydroxide is potassium hydroxide.

7. The process according to claim 1, wherein the PPh$_3$ suspension and the Rh(III) chloride precursor solution are mixed discontinuously in accordance with step (b), wherein the Rh(III) chloride precursor solution is added to the PPh$_3$ suspension already present.

8. The process according to claim 1, wherein sparging with CO gas is carried out at standard pressure.

9. The process according to claim 1, wherein step (c), the stirring of the reaction mixture of PPh$_3$ suspension and Rh(III) chloride precursor at an elevated temperature, is carried out for a period of 1.5 to 3 hours.

10. The process according to claim 1, wherein step (f), the stirring of the reaction suspension, is carried out for a period of 1.5 to 3 hours at a temperature of 40-50° C.

11. The process according to claim 1, wherein step (g), sparging with CO gas, is carried out for a period of 2 to 16 hours.

12. The process according to claim 1, wherein in step (h), the end product, RhH(CO)(PPh$_3$)$_3$, is washed with an alcohol, water or a combination thereof.

13. The process according to claim 1, wherein the alcohol for preparing the alcoholic suspension of triphenylphosphine PPh$_3$ is selected from the group consisting of methanol, ethanol, n-propanol, 2-propanol and mixtures thereof.

* * * * *